United States Patent [19]

Heimberger

[11] Patent Number: 4,643,190

[45] Date of Patent: Feb. 17, 1987

[54] MEDICAL FORCEPS

[75] Inventor: Rudolf Heimberger, Oberderdingen, Fed. Rep. of Germany

[73] Assignee: Richard Wolf GmbH, Fed. Rep. of Germany

[21] Appl. No.: 746,641

[22] Filed: Jun. 20, 1985

[30] Foreign Application Priority Data

Jun. 23, 1984 [DE] Fed. Rep. of Germany ... 8418993[U]

[51] Int. Cl.[4] ............................................. A61B 17/28
[52] U.S. Cl. .................................. 128/321; 128/305; 81/57.39
[58] Field of Search ............... 128/321, 305, 310, 319; 30/240; 81/57.39, 57.29

[56] References Cited

U.S. PATENT DOCUMENTS 2,953,852  9/1960  Dehn ..................................... 30/240
3,756,090  9/1973  Mella et al. ......................... 81/57.39
4,258,716  3/1981  Sutherland ............................ 128/321

FOREIGN PATENT DOCUMENTS 134251  3/1985  European Pat. Off. ............ 128/305

*Primary Examiner*—Gene Mancene
*Assistant Examiner*—John G. Weiss

[57] ABSTRACT

Medical forceps for example for excision of tissue in arthroscopic applications, comprises a jaw element rigidly connected to a shaft and a movable jaw element which is operated via a rotary rod extending through the shaft and a first bevel gear secured to the rod within a proximal housing. The first gear meshes with a second bevel gear which is rotated by an operating lever, via a push rod and a radial lever arm connected to the second bevel gear.

8 Claims, 2 Drawing Figures

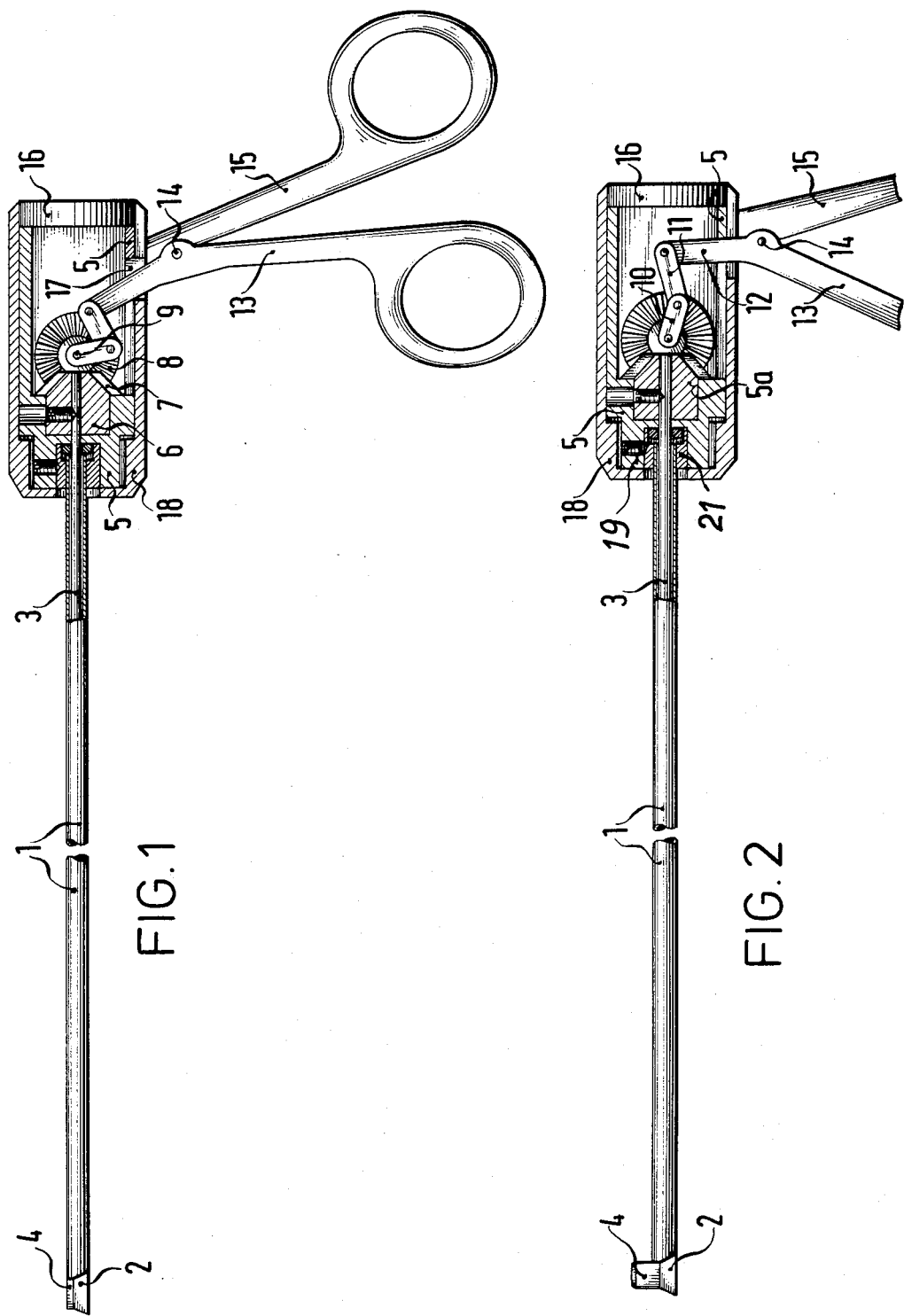

MEDICAL FORCEPS

BACKGROUND OF THE INVENTION

1. Field of the Invention

The invention relates to medical forceps, in particular for arthroscopic application, wherein a fixed jaw element situated at the distal extremity of a shaft has cooperation with it a movable jaw element which is actuated via a rotary rod extending through the shaft and a gear within a proximal housing by means of operating handles.

2. Description of the Prior Art

Such forceps operated by means of operating handles for the purpose of excising tissue or the like are known, in which connection the procedure followed in an embodiment according to the German Utility Model No. 83 11 392 is such that the rigid branch of the operating handle is equipped with a guided toothed bar or rack which is coupled to the movable handle via a link. The rack is entrained by actuation of this handle and operates a proximal gear situated on the rotary rod, whereby the movable distal jaw element is operated for removal of tissue. Because of the exposed rack, soiling of the moving parts may occur and the functionality may be restricted thereby. In the case of other clippers or forceps, the disadvantage again arises that they require comparatively high production costs because of their structure.

SUMMARY OF THE INVENTION

It is an object of the invention to produce a medical cutter or forceps, particularly for arthroscopic applications which is simple and economical to produce and in which all operating elements are protected against soiling and failure.

According to the invention, this object is achieved in the case of the medical forceps referred to in the foregoing in that the rotary rod carries a bevel gear within a proximal housing, which bevel gear meshes with a second bevel gear installed on a transverse spindle, which second bevel gear has a radial lever arm articulated on the one extremity of a push rod, whose other extremity is jointedly coupled to the upper arm of the movable operating handle.

All the parts essential to uncomplicated entrainment of the movable jaw element are thus situated within a housing in a protected manner.

BRIEF DESCRIPTION OF THE DRAWINGS

FIG. 1 shows a longitudinal cross-section of a pair of medical forceps according to the invention with the forceps jaws in the closed position, FIG. 2 shows the same longitudinal cross-section, but with the jaws open.

DETAILED DESCRIPTION OF THE PREFERRED EMBODIMENTS

The medical forceps comprise a tubular shaft 1 with a fixedly attached jaw element 2 firmly joined to its distal extremity. A rotary rod 3 extends through the shaft 1 and has attached to its distal end a movable jaw element 4. At its proximal end, the shaft 1 passes into a housing 5, and the rotary rod 3 is secured by a grub or set screw in a hub 6 of a bevel gear 7. The rotary rod 3 passes through a rotary bearing 21 at the proximal end of the shaft 1. The shaft 1 is secured in the proximal housing 5 in a replaceable manner by means of a grub or set screw 19, and the housing 5 has installed in it a second bevel gear 8 mounted on a transverse spindle or axle 9 and meshing with the gear 7. The bevel gear 8 is coupled to a radial lever arm 10 which is articulated on one end of a push rod 11. The other end of the link or push rod or link 11 is coupled to the upper arm 12 of the movable operating handle 13, which is pivotally attached by a spindle 14 to a second operating handle 15 which in turn is rigidly mounted on the housing 5.

The gear 8 is rotated via the push rod 11 and the lever arm 10 by opening (i.e. pushing apart) the operating handles 13, 15 and thereby turns the gear 7 and the rotary rod 3 to open the forcep jaws 2, 4. For removal of tissue, the jaws 2,4 are closed by pressing the handles 13, 15 together (FIG. 1).

According to the drawings, the hub 6 of the bevel gear 7 is installed or journalled in a cylindrical recess 5a of the housing 5 which is rigidly joined to the operating handle 15. According to FIGS. 1 and 2, the housing 5 is enclosed by means of covers 16, 18. The passage 17 for the movable handle 13, which passes through the housing 5 and the external cover 18, may be sealed by means of elastic covers.

I claim:

1. Medical forceps comprising a hollow shaft having proximal and distal ends, a fixed jaw element being attached to the distal end of said shaft, a housing receiving the proximal end of said shaft, a rotary rod extending through said shaft and having proximal and distal ends with the proximal end extending into the housing, a movable jaw element being attached to the distal end of said rod to cooperate with said fixed jaw element, at least one operating handle on said housing to actuate said movable jaw element, a first bevel gear being attached to the proximal end of the rod, a second bevel gear being mounted in the housing to mesh with the first bevel gear and for rotation about an axis transverse to the axis of rotation of said first gear, said second gear being connected to and rotatable by a radial lever arm pivotally connected to one end of a push rod which in turn is pivotally connected to a pivot arm of said operating handle so that actuation of the operating handle causes rotation of the rod to actuate the movable jaw element.

2. Medical forceps as claimed in claim 1, wherein said first bevel gear has a hub secured releasably to the rotary rod and is journalled in a cylindrical recess within the housing.

3. Medical forceps as claimed in claim 2, wherein a distal section of the housing is releasably connected to the proximal extremity of said shaft.

4. Medical forceps as claimed in claim 1, wherein the housing is closable by means of external covering elements.

5. Medical forceps as claimed in claim 1, wherein the proximal ends of the shaft and the rotary rod are releasably received within the housing to enable them and their respective jaw elements to be replaced.

6. Medical forceps according to claim 1, wherein the rotary rod is journalled in said shaft in a freely rotatable and sealed manner.

7. Medical forceps as claimed in claim 1 wherein said operating handle is pivotally connected to a fixed handle mounted on said housing.

8. Medical forceps comprising:
   a housing;

a tubular shaft having a proximal end releasably secured in said housing, said shaft having a distal end;

a fixed jaw element at the distal end of said tubular shaft;

a rotary rod passing axially through said tubular shaft and through a rotary bearing at the proximal end of said shaft; said rod having a distal end and a proximal end, said proximal end of the rod being releasably secured in a hub of a first bevel gear within said housing;

a movable jaw element at the distal end of said rotary rod, said movable jaw element being arranged to cooperate with said fixed jaw element upon rotation of said rod;

a second bevel gear being mounted within said housing on a spindle for rotation about an axis transverse to the axis of rotation of said first bevel gear and to mesh with said first bevel gear;

a radially extending lever arm being coupled to the said second bevel gear and rotatable therewith;

a push rod being pivotally connected at one end to a radially outer portion of said lever arm and at its other end to one end of a movable operating handle; and a fixed handle secured to said housing, said movable handle being pivotally attached to said fixed handle whereby angular movement of said handles relative to one another causes rotation of said second bevel gear to rotate said first bevel gear, rotary rod and movable jaw element.

* * * * *